United States Patent [19]

Pollock et al.

[11] Patent Number: 5,213,803
[45] Date of Patent: May 25, 1993

[54] ANTIVIRAL COMPOSITION AND METHOD

[75] Inventors: Jerry J. Pollock, Nesconset, N.Y.; John J. Docherty, Kent, Ohio

[73] Assignee: Northeastern Ohio Universities College of Medicine, Rootstown, Ohio

[21] Appl. No.: 840,321

[22] Filed: Feb. 24, 1992

Related U.S. Application Data

[63] Continuation-in-part of Ser. No. 592,552, Oct. 4, 1990, Pat. No. 5,185,153.

[51] Int. Cl.$^5$ .............................................. A61K 9/68
[52] U.S. Cl. .................................. 424/440; 424/430; 424/436; 424/609; 424/663; 424/686; 514/855; 514/934; 514/966; 514/967
[58] Field of Search .............. 424/440, 609, 663, 686, 424/430, 436; 514/934, 855, 966, 967

[56] References Cited

U.S. PATENT DOCUMENTS

| | | | |
|---|---|---|---|
| 3,956,480 | 5/1976 | Dichter et al. | 424/54 |
| 4,661,493 | 4/1987 | Gibbs | 514/252 |
| 4,759,925 | 7/1988 | Gaffar et al. | 424/52 |
| 4,861,582 | 8/1989 | Pollock et al. | 424/52 |
| 4,863,900 | 9/1989 | Pollock et al. | 514/12 |
| 4,915,936 | 4/1990 | Patterson et al. | 424/49 |
| 4,950,479 | 8/1990 | Hill et al. | 424/79 |
| 4,980,150 | 12/1990 | Keith | 424/49 |
| 4,981,875 | 1/1991 | Leusner et al. | 514/774 |

OTHER PUBLICATIONS

Yash et al., *American Clinical Laboratory*, 23-32 (Oct. 1990).
Park et al., *Oral Surg. Oral Med. and Oral Path.*, 67, 149-153 (1989).
Zimmerman et al, *J. Med. Virol.*, 15, 215-222 (1985).
McCaughtry et al, *J. Med. Virol.*, 10, 283-290 (1982).
DeClerq et al, *Proc. Nat. Acad. Sci. USA*, 76, 2947-2951 (1979).
Docherty et al., *Proc. Soc. Exp. Biol. Med.*, 136, 328-333 (1971).
Hoxie, et al., *Science*, 234, 1123-1127 (1986).

*Primary Examiner*—Thurman K. Page
*Assistant Examiner*—D. Gabrielle Phelan
*Attorney, Agent, or Firm*—Hoffmann & Baron

[57] ABSTRACT

A method utilizing compositions for topical application which are adapted for the prevention and treatment of viral infections such as Herpes, AIDS and other envelope virus infections are disclosed. The compositions of the present invention produce a synergistic anti-viral effect when used in combination. The formulation contains a humectant such as sorbitol, glycerol, or other comparable compound in the range of 20-80% w/v final concentration, which facilitates structural and/or functional three dimensional disruption or disorientation of the viral envelope. The activation of the destruction of the envelope and subsequent death of the envelope virus is then achieved using combination of inorganic monovalent anions, nonionic detergents and anionic detergents. These monovalent anions can include sodium bicarbonate, sodium thiocyanate, sodium fluoride and sodium chloride at about 0.5 to 5% w/v final concentration; nonionic detergents such as Tween 20 at concentrations of about 0.1% to 3% v/v, ethanol up to about 15% v/v, and other antimicrobial agents such as chlorhexidine or comparable basic substances at concentrations from about 0.01 to 0.2% v/v. The formulation may also include anionic surfactants, flavor and water added to 100%.

24 Claims, No Drawings

ANTIVIRAL COMPOSITION AND METHOD

This is a continuation-in-part of copending application Ser. No. 07/592,552 filed on Oct. 4, 1990, now U.S. Pat. No. 5,185,153.

BACKGROUND OF THE INVENTION

1. Field of the invention

The present invention relates to topical composition and methods for the prevention and treatment of viral infections, such as Herpes and AIDS.

2. Background of the Related Art

Sexually transmitted diseases such as Herpes and AIDS remain frustrating, distressing and unyielding infections. Patients continually suffer their disease and in the case of AIDS, the patient ultimately succumbs and gives up his or her life. Because these diseases socially brand patients once they are infected with these envelope viruses, it is not only important to reduce the level of these viruses in the infected patients, but it is also important to protect non-infected individuals from acquiring these viruses. Thus in one case, treatment is necessary to stabilize the patients while in non-infected individuals, prevention is imperative.

At the present time, there are a limited number of small molecular weight drugs which are either being used therapeutically or are currently being tested in antiviral chemotherapy. The majority of these drugs are derivatives of nucleosides, although in recent years with the development of AIDS, other types of drugs, for example, peptides have been undergoing rigorous testing as potential antivirals. The peptides are geared to block viral penetration of human cells while the nucleosides exert their antiviral effects by penetrating viral-infected mammalian cells, thus interfering inside the cell with nucleic acid synthesis.

To date, the failures of antiviral chemotherapy can be attributed in part to a lack of selective toxicity, in part to the development of chronic resistance to antiviral drugs and in part to the recurrence of infection once drug therapy has been terminated. In the case of Herpes, recurrence of infection is exacerbated by the latency of the virus which emerges insidiously from its home in the ganglia of nerve cells to cause infection. This is also true for the HIV-1 virus (the AIDS virus) which not only hides in an inactive form in the host chromosome but also is proving more and more elusive and resistant even when patients are given powerful drugs such as azidothymidine (AZT).

As an alternative to prescription antiviral drugs which have toxic side effects, it would be desirable to develop an inexpensive, safe combination of simple ingredients that would be used as a potent over-the-counter antiviral formulation. Although a number of simple chemicals will inactivate both the Herpes and AIDS virus, as well as other viruses, these chemicals for the most part are not safe for human use and are generally employed for the disinfection of biological samples and tissue; See for example Yash et al., *American Clinical Laboratory*, 23–32 (October 1990).

To protect both infected and non-infected individuals, it is the belief of the inventors, herein, that a daily regimen of an appropriate antiviral formulation is required Since it is believed that this formulation should be given long-term on a continuous basis without interruption, then a simple safe over-the-counter formulation would be ideal for both treatment and prevention of viral disease. In the case of a mouthrinse, which has only a limited time period in the oral cavity, antiviral activity should be accomplished within a minute of contact with virus. This would also be true of vaginal douches, but would be less important, for example, with vaginal and rectal creams which can be formulated to remain longer at the site of the infection.

Chlorhexidine at 0.2% is known as being an effective antibacterial germicidal and has been shown to exert moderate Herpes antiviral activity, Park et al., *Oral Surg. Oral Med. and Oral Path.*, 67, 149–153 (1989). However, Chlorhexidine has an unpleasant bitter taste and characteristically stains both tooth enamel and skin a brown color. Very dilute concentrations of chlorhexidine, i.e. about 0.05% on the other hand, are not known to be effective anti-viral agents.

Various compositions containing chlorhexidine are present in the prior art. For example, chlorhexidine is contained in an oral rinse germicidal composition sold under the name PERIDEX ®. It contains a 0.12% chlorhexidine gluconate in a base containing water, 11.6% alcohol, glycerine, PEG-40 sorbitan disostearate, flavor, sodium saccharine, and FD&C Blue No. 1. There are a various patents which describe the use of Chlorhexidine for its antibacterial/antifungal germicidal activity, see U.S. Pat. Nos. 3,956,480, 4,759,925, 4,915,936, and 4,980,150.

Other compositions that are described as being antiviral, specifically the treatment of herpes virus infection are disclosed in U.S. Pat. No. 4,661,493 to Gibbs. Gibbs describes topical vaginal forms of tioconazole and related antimicrobic compounds, especially miconazole, econazole, clotrimazole, butaconazole and ketoconazole for being useful in controlling Herpes virus infections. A variety of representative formulations are described on Col. 4 of the patent, for example tioconazole vaginal tablets containing 100mg per tablet of tioconazole and 1.20mg per tablet of sodium lauryl sulfate in a total formulation weighing 1,128mg. Tioconazole cream containing propylene glycol, ointment containing tioconazole and paraffin, and tioconazole vaginal ovals containing tioconazole and glycine as the primary components are also described.

The inventors herein in U.S. Pat. No. 4,863,900 describe a method for reducing viral transmission of HSV-1 and HSV-2 infections using compositions containing poly-L-histidine. The compositions include a topically applicable, pharmaceutically acceptable carrier and a viricidally effective amount of a polypeptide of between 24 and 500 aminoacid residue; containing at least 24 residues of L-histidine. These compositions are described as generally applicable to Herpes infections of the mucosa, such as eye infection, oral infection and vaginal infection; and viral infection of non-mucosa tissues, in particular border areas such as lips and rectum as well as the skin. The patent recites that all envelope viruses are considered within the scope of the invention but especially herpes simplex virus such as HSV-1 or HSV-2. A variety of formulations containing the poly-L-histidine compound in approximately a 10% concentration are disclosed at columns 4–10 of the patent. For example, a toothpaste formulation is described as containing poly-L-histidine, carboxymethyl cellulose, glycerine, propylene glycol and sodium lauryl sulfate; and a mouthwash formulation is described as containing approximately 10% poly-L-histidine and approximately 10% each glycerine and water. Poly-L-histidine is the active anti-herpes antiviral agent of this patent and without it the composition lacks any antiviral activity. More importantly, poly-L-histidine is not effective against the AIDS virus.

Other medicaments described as useful for the treatment of bacterial, viral or fungicidal inflammation of the oral cavity are disclosed in U.S. Pat. No. 4,981,875 to Lausner et al. The medicaments described by Lausner et al. are adhesive emulsions containing etofenate, a suitable carrier, a swellable hydrophilic polymer, flavorings, preservatives and colorants, as well as other active compounds which can be included, such as anesthetics chemotherapeutics, antibiotics, disinfectants and astringents. The effectiveness of this medicament in the treatment of viral infections such as Herpes, AIDS and other envelope virus infections is not disclosed.

Accordingly, there is an urgent need for topical compositions and methods for the prevention and treatment of envelope viral infections such as Herpes and AIDS, which can be applied topically without the above-mentioned drawbacks of the compositions of the prior art.

SUMMARY OF THE INVENTION

These and other needs are satisfied by the present invention which provides a method utilizing composition for topical application which are adapted for the prevention and treatment of viral infections such as Herpes, and other envelope virus infections. Primarily, these compositions are for application to the oral, vaginal and rectal cavities, as well as surrounding tissue. It is proposed, however, that these compositions can also be of use in other parts of the organism, for example to the lips in treatment of cold sores, to the skin for the treatment of Herpes infections and to the surrounding skin of the penis, vagina or rectum for treatment and prevention of AIDS and Herpes infections. Furthermore these compositions can be used for the treatment of surfaces and instruments that may come in contact with the animal or human body, for example professionally by a restorative dentist, periodontist in the operation of high speed hand pieces, or as a safe anti-viral disinfectant in a clinical environment.

The ingredients of the present invention produce synergistic anti-viral effect when used in combination. The formulation contains a humectant such as sorbitol, glycerol, or other comparable compounds which facilitate structural and/or functional three dimensional disruption or disorientation of the viral envelope to permit the remaining ingredients of the formulation to penetrate the virus and affect rapid and irreversible destruction which kills the virus. The humectant should probably be used in the range of 20-80% w/v final concentration, preferably about 30% to 50% w/v final concentration, most preferably glycerol at about 40% w/v final concentration, or sorbitol at about 30% w/v final concentration. Activating the destruction of the envelope and the subsequent death of the envelope virus is achieved using a combination of inorganic monovalent anions, nonionic detergents and anionic detergents. These monovalent anions can include sodium bicarbonate, sodium thiocyanate, sodium fluoride and sodium chloride at about 0.5 to 5% w/v final concentration. The other ingredients include nonionic detergents such as Tween 20 at concentrations of about 0.1% to 3% v/v, ethanol up to 15% v/v and other antimicrobial agents can also be included, such as chlorhexidine or comparable basic substances at about 0.01 to 0.2% v/v. The compositions of the present invention also may include anionic surfactant detergent in a concentration of about 0.01 to about 3%, flavor and water added up to 100%.

The compositions of the present invention can be conventionally formulated to mouthrinses, lip-balms, mouthsprays, toothpastes, dental creams, chewable carriers such as chewing gums, lozenges, breath fresheners and candies, vaginal creams and vaginal careproducts, rectal suppositories, ointments and creams and spermicidal jellies. The mouthrinse formulations may be used professionally, for example by restorative dentists or periodontists in the operation of high speed hand pieces, or as a safe anti-viral disinfectant in clinical environments.

For a better understanding of the present invention, reference is made to the following description and examples taken in conjunction with the accompanying tables, the scope of which is pointed out in the appended claims.

DETAILED DESCRIPTION OF THE INVENTION

The present invention relates to compositions that are applied topically and adapted for prevention and treatment of Herpes, AIDS and other envelope viral infections. Primarily, the use of these compositions is for application to the oral, vaginal and rectal cavities. It is suggested, however, that these compositions would also be of use in other parts of the body, for example, to the lips in the treatment of cold sores or to the skin for treatment of Herpes infections of the skin.

The compositions of the present invention contain ingredients which by themselves are not potent antivirals when tested in solution for a one minute treatment period. Remarkably, however, a rapid synergistic antiviral effect is noted when these ingredients are used in combination. Moreover, the most potent antiviral activity occurs when all ingredients are used together (greater than 99.9% inactivation). The formulation contains a humectant such as sorbitol, glycerol or other comparable compounds. Although the inventors do not wish to be bound by their hypothesis, it is suggested that the humectant acts as a facilitator causing structural and/or functional three-dimensional disruption or disorientation of the viral envelope, thus permitting the other ingredients of the formulation to penetrate the virus and effect rapid irreversible destruction. Since the findings given in the examples, herein, indicate loss of viral inhibitory activity as the concentration of the facilitator (humectant) is decreased, it is suggested that the humectant should preferably be used in a range of 20% to 80% w/v final concentration. Activation of cell death of the envelope viruses is then achieved using a combination of inorganic monovalent anions (for example, sodium bicarbonate, sodium thiocyanate, sodium fluoride and sodium chloride) at 0.5% to 5% w/v final concentration, ethanol up to 15% v/v, non-ionic detergents such as Tween 20 at 0.1% to 3% v/v and antimicrobial agents such as chlorhexidine or comparable basic substances at 0.01 to 0.2% v/v. The compositions of the present invention also may include anionic surfactants, flavor and water added to 100 percent.

The compositions according to the present invention may be incorporated in a manner and vehicle suitable for oral, vaginal or rectal cavity administration. Also the composition of the present invention can be conventionally formulated into mouthrinses, lip-balms, mouthsprays, toothpastes, dental creams, chewable carriers such as gums, lozenges, breath fresheners and candies, vaginal creams and vaginal care-products, rectal suppositories, ointments and creams and spermicidal jellies. The mouthrinses may be used professionally, for example, by a restorative dentist or periodontist in the operation of their high speed handpieces, or as a safe antiviral disinfectant in a clinical environment.

The properties of the composition of the present invention are determined both from tissue culture studies and by in vivo testing in mice. Viruses are reacted with the compositions for a period of 1 minute in vitro experiments after which they are tested for their ability to infect and multiply in standardized tissue culture cell lines. In vivo experiments, antiviral activity is tested in mice after a similar 1 minute treatment of the virus with the composition of the present invention.

Although the focus of this invention is to use the formulation hereto mentioned for inactivating envelope viruses, the Inventors do not wish to be bound only to these viruses as the formulation may well destroy all viruses. Envelope viruses have been studied mainly for two reasons: first, Herpes infection can be seriously debilitating while AIDS we know to be fatal and second, the inventors hypothesize that the mechanism of action of these formulations may be in altering the envelope of the virus followed by penetration of agents which then destroy the virus.

EXAMPLES

I. In Vitro Studies

A. Material and Methods

Herpes: Herpes simplex virus type 1 (HSV-1) tissue culture studies were employed to assess the effects of the mouthrinses on Herpes viruses. Monkey kidney cells (VERO) were grown and maintained in Medium 199 (Flow Laboratories, Inc. McLean, VA) supplemented with 5% calf serum, 50 ug gentamycin per ml and 0.75% $NaHCO_3$.

Laboratory strains of HSV-1 were used throughout. The type designation of the virus was authenticated by indirect monoclonal antibody immunofluorescence in accordance with Zimmerman et al, *J. Med. Virol.*, 15, 215-222 (1985), restriction endonuclease patterns as described by McCaughtry et al, *J. Med. Virol.*, 10, 283-290 (1982) and sensitivity to (E)-5-(2-bromovinyl)-2'-deoxyuridine in accordance with DeClerg et al, *Proc. Nat. Acad. Sci. USA*, 76, 2947-2951 (1979).

The inactivating effect of the mouthrinses on virus was investigated as follows. Ingredients of the mouthrinse were dissolved in medium 199 and the pH was adjusted to pH 8. Approximately $10^5$ plaque forming units (PFU) of virus was combined with the mouthrinses and the mixtures were incubated at room temperature for exactly 1 min. Viral titers were then determined in Vero cells as described Docherty et al., *Proc. Soc. Exp. Biol. Med.*, 136, 328-333 (1971).

II. AIDS

The inactivating effect of the mouthrinse on HIV-1 (AIDS virus) was investigated as follows. The chemical stocks were added to Medium 199 to obtain the specified concentrations, and the pH was adjusted to 8.0 using $NaHCO_3$. Control solutions consisted of Medium 199 also at pH 8.0. Approximately $1.5 \times 10^4 - 1.5 \times 10^5$ infectious units of HIV-1 in 0.15 ml were added to 1.35 ml of the test compound and incubated for one minute at room temperature. The amount of viable virus after exposure to the mouthrinses was determined by the cytopathic effect (CPE) in SupT1 cells as described by Hoxie, et al., *Science*, 234, 1123-1127 (1986).

III. In vivo Studies

Animals: All animal studies involved male BALB/c mice of approximately 8 to 10 weeks of age. There were three groups of six mice each. Group 1 was the control group which were injected in the soft tissue of the left mandible with untreated HSV-1 virus (approximately $1 \times 10^5$ PFU). Group 2 was injected as described for Group 1, with virus that was treated for 1 minute with a mixture of 30% sorbitol, 1% Tween 20, 1.5% $NaHCO_3$, 0.5% NaScN, and 7% ethanol. Group 3 was injected as described for Group 1, with virus that was treated for 1 minute with a mixture of 30% sorbitol, 0.05% chlorhexidine, 1.5% $NaHCO_3$, 0.5% NaSCN and 7% ethanol. The animals were observed daily for signs of viral infection.

IV. RESULTS

Example 1

Table 1 shows the effects of various mouthrinse ingredients of the present invention on the inactivation of HSV-1 infectivity.

TABLE 1

Effects of Mouthrinse Ingredients on Anti-Herpes Infectivity

| Mouthrinse | Plaque Forming Units 1-Minute Exposure | Percent Inactivation |
|---|---|---|
| Control* | $1.2 \times 10^5$ | — |
| 1.5% $NaHCO_3$** 0.5% NaSCN | $1.2 \times 10^5$ | 0 |
| 30% Sorbitol 1.5% $NaHCO_3$ 0.5% NaSCN | $1.2 \times 10^5$ | 0 |
| 30% Sorbitol 1.5% NaHCO 0.5% NaSCN 7.0% Ethanol | $1.2 \times 10^5$ | 0 |
| 1% Tween 20 | $1.0 \times 10^5$ | 8.3 |
| 1% Tween 20 30% Sorbitol | $3.0 \times 10^4$ | 83.3 |
| 1% Tween 20 1.5% $NaHCO_3$ 0.5% NaSCN 7.0% Ethanol | $1.7 \times 10^3$ | 98.6 |
| 30% Sorbitol 1% Tween 20 1.5% $NaHCO_3$ 0.5% NaSCN 7.0% Ethanol | $<1.0 \times 10^2$ | >99.9 |

*Control was Herpes virus in Medium 199.
**All ingredients were dissolved in Medium 199.

Table 1 demonstrates that Herpes simplex type 1 virus is not inactivated by combinations of inorganic salts+sorbitol, or inorganic salts+sorbitol+alcohol. Tween 20 by itself also has little effect, if any, on the virus. In terms of percent inhibition, Tween 20+sorbitol does have an effect within one minute but a large number of viral particles (about 30,000 PFU) still remain after the treatment. In the absence of sorbitol, increased inhibition is noted with salts+Tween+alcohol. However, by far the most potent antiviral activity (>99.9% inhibition) is seen only when all five ingredients (sorbitol, Tween 20, $NaHCO_3$, NaSCN and alcohol) are tested in tissue culture.

Example 2

Table 2 shows the effect of replacing Tween 20 with Chlorhexidine gluconate in the mouthrinse formulation of the present invention.

TABLE 2

Effect of Chlorhexidine and Chlorhexidine Containing Mouthrinses on Anti-Herpes Infectivity

| Mouthrinse | Plaque Forming Units 1-Minute Exposuure | Percent Inactivation |
|---|---|---|
| Control | $1.8 \times 10^5$ | — |
| 0.05% Chlorhexidine | $7.4 \times 10^4$ | 59.0 |
| 0.05% Chlorhexidine 1.5% NaHCO$_3$ 0.5% NaSCN 7.0% Ethanol | $9.5 \times 10^4$ | 47.2 |
| 30% Sorbitol 0.05% Chlorhexidine 1.5% NaHCO$_3$ 0.5% NaSCN 7.0% Ethanol | $<1.0 \times 10^2$ | >99.9 |

Table 2 demonstrates that a similar potent antiviral activity is noted only when chlorhexidine gluconate is combined with sorbitol, NaHCO$_3$, NaSCN and alcohol In the absence of sorbitol, a significant inhibitory activity is not seen.

Example 3

Table 3 demonstrates the effect of sorbitol concentration on the antiviral activity of the Tween 20 containing mouthrinse of the present invention.

TABLE 3

Effect of Sorbitol Concentration on Anti-Herpes Activity of a Tween Containing Mouthrinse

| Mouthrinse | Plaque Forming Units 1-Minute Exposure | Percent Inactivation |
|---|---|---|
| Control | $1.4 \times 10^5$ | — |
| Basic Mouthrinse* + 30% Sorbitol | $<1.0 \times 10^2$ | >99.9 |
| Basic Mouthrinse* + 20% Sorbitol | $<1.0 \times 10^2$ | >99.9 |
| Basic Mouthrinse + 10% Sorbitol | $1.5 \times 10^2$ | 99.9 |
| Basic Mouthrinse + 1% Sorbitol | $2.5 \times 10^2$ | 99.9 |
| Basic Mouthrinse + 0.1% Sorbitol | $2.5 \times 10^2$ | 99.9 |

*The Basic Mouthrinse contained 1% Tween 20, 1.5% NaHCO$_3$, 0.5% NaSCN and 7.0% ethanol dissolved in Medium 199.

As shown in table 3, in the Tween 20 mouthrinse formulation of the present invention, reducing the sorbitol concentration does reduce the effectiveness of the mouthrinse. Even with 0.1% sorbitol, however, the mouthrinse is still very effective, and is an order of magnitude more effective than when sorbitol is absent; for example compare the results shown in Table 1 with Table 3.

Example 4

By contrast to the Tween 20 containing mouthrinses, Table 4 shows that for the chlorhexidine gluconate mouthrinses, reducing the sorbitol concentration dramatically deceases the antiviral potency.

TABLE 4

Dependence of Anti-Herpes Activity on Sorbitol Concentration of a Chlorhexidine Containing Mouthrinse

| Mouthrinse | Plaque Forming Units 1-Minute Exposure | Percent Inactivation |
|---|---|---|
| Control | $1.4 \times 10^5$ | — |
| Basic Mouthrinse* + 30% Sorbitol | $<1.0 \times 10^2$ | >99.9 |
| Basic Mouthrinse* + 20% Sorbitol | $1.9 \times 10^4$ | 87.0 |
| Basic Mouthrinse* + 10% Sorbitol | $4.8 \times 10^4$ | 66.0 |
| Basic Mouthrinse* + 1% Sorbitol | $1.2 \times 10^5$ | 19.0 |
| Basic Mouthrinse* + 0.1% Sorbitol | $1.7 \times 10^5$ | 0 |

*The Basic Mouthrinse contained 0.05% chlorhexidine gluconate, 1.5% NaHCO$_3$, 0.5% NaSCN and 7.0% ethanol dissolved in Medium 199.

As shown in Table 4, at 0.1% concentration no inhibition by the mouthrinse was observed. In order to maintain full potency (>99.9% inhibition) a concentration of at least 30% sorbitol or greater is required.

Example 5

Table 5 shows the results of the animal in vivo studies described in section "III." above. The animal data was collected during a one week observation period. It was observed that mice that were injected with HSV-1 after the virus was exposed to either of the two formulations according to the present invention for one minute (groups 2 and 3) were much less likely to develop an infection than the mice that were injected with the untreated HSV-1 virus control.

TABLE 5

Animal Studies

| Treatment Group | Mouse Number | Days After Treatment | | | | | | |
|---|---|---|---|---|---|---|---|---|
| | | 1 | 2 | 3 | 4 | 5 | 6 | 7 |
| Group 1+ | 1 | 0* | 0 | .5 | 1 | 1 | 1 | 1 |
| | 2 | 0 | 0 | 0 | 1 | 1 | 1 | 1 |
| | 3 | 0 | 0 | 1 | 1 | 1 | 1 | 2 |
| | 4 | 0 | 0 | .5 | .5 | 1 | 1 | 1 |
| | 5 | 0 | 0 | 0 | 0 | .5 | 1 | 1 |
| | 6 | 0 | 0 | 0 | .5 | 1 | 1 | 1 |
| Group 2 | 7 | 0 | 0 | 0 | 0 | 0 | 0 | .5 |
| | 8 | 0 | 0 | 0 | 0 | 0 | 0 | 0 |
| | 9 | 0 | 0 | 0 | 0 | 0 | 0 | .5 |
| | 10 | 0 | 0 | 0 | 0 | 0 | 0 | 0 |
| | 11 | 0 | 0 | 0 | 0 | 0 | 0 | 0 |
| | 12 | 0 | 0 | 0 | 0 | 0 | 0 | 0 |
| Group 3 | 13 | 0 | 0 | 0 | 0 | 0 | 0 | 0 |
| | 14 | 0 | 0 | 0 | 0 | 0 | 0 | 0 |
| | 15 | 0 | 0 | 0 | 0 | 0 | 0 | 0 |
| | 16 | 0 | 0 | 0 | 0 | 0 | .5 | 1 |
| | 17. | 0 | 0 | 0 | 0 | 0 | 0 | 0 |
| | 18. | 0 | 0 | 0 | 0 | 0 | 0 | 0 |

+Group 1 = mice injected with untreated HSV-1 virus control; Group 2 = mice injected with HSV-1 virus treated for one minute with 30% sorbitol, 1% tween 20, 1.5% NaHCO$_3$, 0.5% NaSCN and 7% ethanol; Group 3 = mice injected with HSV-1 virus treated for one minute with 30% sorbitol, 0.05% chlorhexidine, 1.5% NaHCO$_3$, 0.5% NaSCN and 7% ethanol.
*0 = no disease; 1 = closed eyes; 2 = closed eyes plus ruffled hair.

Example 6

Table 6 demonstrates that the mouthrinse formulations of the present invention are completely effective against HIV-1, the AIDS virus.

TABLE 6

Effect of Sorbitol and Chlorhexidine Mouthrinses on the AIDS Virus

| Mouthrinse | Cytopathic Effect (CPE 1-Minute Exposure | Percent Inactivation |
|---|---|---|
| Control | 3-4+ | — |
| Basic Mouthrinse* + 1% Tween 20 | 0 | 100 |
| Basic Mouthrinse + 0.05% Chlorhexidine | 0 | 100 |

*The Basic Mouthrinse contained 1.5% NaHCO$_3$, 0.5% NaSCN, 7% ethanol and 30% sorbitol dissolved in Medium 199.

Example 7

A preferred Tween 20 containing mouthrinse in accordance with the present invention is shown in Table 7.

TABLE 7

Tween Mouthrinse Formulation

| Component | Concentration |
|---|---|
| Sorbitol | 80 gm |
| Sodium Bicarbonate | 3 gm |
| Sodium Thiocyanate | 1 gm |
| Sodium Lauryl Sarcosinate | 1 gm |
| Tween 20 | 3 ml |
| Alcohol | 15 ml |
| Pluronic F127 | 0.012 gm |
| Oil of Peppermint | 0.1 ml |
| Water q.s. | 100 ml |

The mouthrinse formulation shown in Table 7 is utilized by rising the mouth for about 30 to 60 seconds from 1-3 times per day with about 15 ml of undiluted mouthrinse. The mouthrinse can be used as a home regimen intracrevicular wash by placing the formulation in a WATER-PIK ® type instrument. It can also be dispensed to patients by the dentist or periodontist when they treat patients with high speed handpieces.

Example 8

A preferred chlorhexidine gluconate contains mouthrinse in accordance with the present invention is shown in Table 8.

TABLE 8

Chlorhexidine Mouthrinse Formulation

| Component | Concentration |
|---|---|
| Sorbitol | 40 gm |
| Sodium Bicarbonate | 3 gm |
| Sodium Thiocyanate | 1 gm |
| Chlorhexidine Gluconate | 0.2 gm |
| Alcohol | 7 ml |
| Pluronic F127 | 0.012 gm |
| Oil of Peppermint | 0.1 ml |
| Water q.s. | 100 ml |

The mouthrinse formulation shown in Table 8 is utilized by rinsing the mouth for about 30 to 60 seconds from 1-3 times per day with about 15 ml of undiluted mouthrinse. The mouthrinse can be used as a home regimen intracrevicular wash by placing the formulation in a WATER-PIK ® Tye instrument. It can also be dispensed to patients by the dentist or periodontist when they treat patients with high speed handpieces.

Example 9

A preferred mouthspray formulation in accordance with the present invention is shown in Table 9.

TABLE 9

Mouthspray Formulation

| Component | Concentration |
|---|---|
| Glycerol | 40 ml |
| Sodium Bicarbonate | 1.5 gm |
| Sodium Thiocyanate | 0.5 gm |
| Sodium Lauryl Sulfate* | 0.5 gm |
| Tween 20 | 1 ml |
| Sodium Saccharin | 0.07 gm |
| Peppermint Spirit | 15 ml |
| Water q.s. | 100 ml |

*Can replace with 0.05 gm of chlorhexidine gluconate. Tween 20 then becomes optional in the formulation.

The mouthspray formulation shown in Table 9 is utilized by spraying aliquots of 0.25 to 0.50 ml onto each quadrant of the gingiva and tooth surface and onto the lips between 1 and 3 times per day.

Example 10

A preferred toothpaste gel formulation in accordance with the present invention is Shown in Table 10.

TABLE 10

Toothpaste Gel Formulation

| Component | Concentration |
|---|---|
| Glycerin | 40 ml |
| Sodium Bicarbonate | 2 gm |
| Sodium Thiocyanate | 1 gm |
| Sodium Lauryl Sarcosinate* | 1 gm |
| Tween 20 | 3 ml |
| Carboxymethyl Cellulose 120H | 1.8 gm |
| Sodium Saccharin (50% soln) | 0.2 ml |
| Oil of Peppermint | 2 ml |
| Mineral Oil | 2 ml |
| Silica | 21 gm |
| Water q.s. | 29 ml |

*Can replace with 0.2 gm of chlorhexidine gluconate. Tween 20 then becomes optional in the formulation.

The toothpaste gel formulation shown in Table 10 is utilized by cleaning the teeth with about 1 to 2 gm of paste between 1 to 3 times per day.

Example 11

A preferred topical vaginal or rectal cream formulation in accordance with the present invention is shown in Table 11.

TABLE 11

Topical Vaginal or Rectal Cream

| Component | Concentration Percent (w/w) |
|---|---|
| Sorbitol | 30 |
| Glycerin | 10 |
| Sodium Bicarbonate | 4 |
| Sodium Thiocyanate | 1 |
| Sodium Lauryl Sarcosinate* | 0.5 |
| Tween 20 | 1 |
| Cetyl Alcohol | 0.5 |
| Stearic Acid | 25 |
| Triethanolamine | 0.2 |
| Methyl Paraben | 0.1 |
| Propyl Paraben | 0.1 |
| Water q.s. | 100% |

*Can replace with 0.2% (w/w) chlorhexidine gluconate. Tween 20 then becomes optional in the formulation.

For topical use the topical vaginal or rectal cream formulation shown in Table 11 can be gently massaged into the affected and surrounding areas twice daily (morning and evening). For intravaginal use, about 5 gm of the cream is applied with applicator high into the vaginal vault once or twice daily. For rectal use, the cream can be applied liberally until adsorbed. Treatment is continued as indicted, until inflammation and lesions are eliminated (usually two to four weeks).

Example 12

A preferred vaginal or rectal suppository formulation in accordance with the present invention is shown in Table 12.

TABLE 12

| Vaginal or Rectal Suppositories | |
|---|---|
| Component | Concentration Percent (w/w) |
| Sorbitol | 20 |
| Glycerin | 20 |
| Polyethylene Glycol 4000 | 20 |
| Polyethylene Glycol 1000 | 20 |
| Tween 20 | 2 |
| Sodium Bicarbonate | 2 |
| Sodium Thiocyanate | 2 |
| Sodium Lauryl Sulfate* | 0.5 |
| Methyl Paraben | 0.1 |
| Propyl Paraben | 0.1 |
| Water q.s. | 100% |

*Can replace with 0.05% (w/w) chlorhexidine gluconate. Tween 20 then becomes optional in the formulation.

The preferred vaginal or rectal suppository formulation shown in Table 10 is used by inserting one 3 gram suppository into the vaginal vault or rectum once or twice daily. Treatment is continued as indicated until inflammation and lesions are eliminated (usually two to four weeks).

Example 13

A preferred vaginal deodorant solution formulation in accordance with the present invention is shown in Table 13.

TABLE 13

| Vaginal Deodorant Solution | |
|---|---|
| Component | Concentration Percent (w/w) |
| Sorbitol | 33 |
| Sodium Bicarbonate | 0.5 |
| Sodium Thiocyanate | 0.5 |
| Sodium Lauryl Sarcosinate* | 0.5 |
| Alcohol | 5 |
| Tween 20 | 0.5 |
| Sodium Acetate | 0.17 |
| Acetic Acid | 0.08 |
| Sodium Chloride | 1 |
| Menthol | 0.25 |
| Thymol | 0.25 |
| Methyl Salicylate | 0.5 |
| Water q.s. | 100% |

*Can replace with 0.05% (w/w) chlorhexidine gluconate. Tween 20 then becomes optional in the formulation.

The preferred vaginal deodorant solution formulation shown in Table 13 is utilized by applying about 200 ml of the solution daily to vaginal mucosal surfaces.

Example 14

A preferred topical vaginal or rectal ointment formulation in accordance with present invention is shown in Table 14.

TABLE 14

| Topical, Vaginal or Rectal Ointment | |
|---|---|
| Component | Concentration Percent (w/w) |
| Propylene Glycol | 12 |
| Stearyl Alcohol | 25 |
| Sorbitol | 20 |
| Alcohol | 5 |
| Sodium Bicarbonate | 4 |
| Sodium Thiocyanate | 3 |
| Chlorhexidine Gluconate | 0.2 |
| White Petrolatum | 25 |
| Methyl Paraben | 0.25 |
| Propyl Paraben | 0.15 |
| Water q.s. | 100% |

*Tween 20, 3% (w/w), can be added into the formulation if desired.

The preferred topical vaginal or rectal ointment formulation shown in Table 14 is utilized by gently massaging the ointment on a daily basis onto the affected and surrounding areas until inflammation and lesions are eliminated.

Example 15

A preferred skin lotion formulation in accordance with the present invention is shown in Table 15.

TABLE 15

| Skin Lotion Formulation | |
|---|---|
| Component* | Concentration Percent (w/w) |
| Sorbitol | 40 gm |
| Ethanol | 10 ml |
| Tween 20 | 2 ml |
| Sodium Bicarbonate | 3 gm |
| Sodium Thiocyanate | 0.5 gm |
| Sodium Lauryl Sulfate* | 0.5 gm |
| Propylene Glycol | 14 ml |
| Triethanolamine | 1 ml |
| Oleic Acid | 1.5 gm |
| Polyethylene Glycol 400 Monostearate | 10.5 gm |
| Silicone Fluid | 10 ml |
| Carbopol | 10 gm |
| Water q.s. | 100 ml |

*Can replace with 0.1% chlorhexidine gluconate. Tween 20 then becomes optional in the formulation.

The preferred skin lotion formulation shown in Table 15 is applied topically by gently massaging the lotion into the affected and surrounding areas of the skin, penis or lips twice daily (morning and evening). Treatment is continued as indicated until lesions are no longer noted.

Example 16

A preferred chewing gum formulation in accordance with the present invention is shown in Table 16.

TABLE 16

| Chewing Gum Formulation | |
|---|---|
| Component | Concentration Percent (w/w) |
| Sodium Bicarbonate | 0.5 gm |
| Sodium Thiocyanate | 0.5 gm |
| Tween 20 | 0.5 ml |
| Sodium Lauryl Sarcosinate | 0.1 ml |
| Estergum | 0.15 gm |
| Coumarin Res | 0.25 gm |
| Latex (dry) | 0.1 gm |
| Paraffin Wax (melting pt. 180° F.) | 0.05 gm |
| Corn Syrup | 0.4 gm |
| Flavor | 0.02 gm |
| Sorbitol q.s. | 3 gm |

The chewing gum formulation shown in Table 16 is utilized as an antiviral agent as needed.

Example 17

A preferred candy (Lozenge) formulation in accordance with the present invention is shown in Table 17.

TABLE 17

| Candy (Lozenge) Formulation | |
|---|---|
| Component | Concentration |
| Sorbitol | 0.6 gm |
| Sodium Bicarbonate | 0.5 gm |
| Sodium Thiocyanate | 0.5 gm |
| Chlorhexidine Gluconate | 0.005 gm |
| Mannitol (powdered) USP | 0.18 gm |
| Sodium Stearate | 0.005 gm |
| Licorice | 0.1 gm |
| Talc | 0.01 gm |
| Capsicum | 0.002 gm |
| Methanol | 0.002 gm |
| Lactose (powdered) USP q.s. | 3 gm | the candy (lozenge) formulation shown in Table 17 is utilized as an antiviral agent as needed.

Thus, while we have described what are the presently contemplated embodiments of the invention, further changes in modifications could be made by those skilled in the art without departing from the scope of the invention, and it is contemplated to claim all such changes and modifications.

We claim:

1. A method for killing envelope virus in vitro causing AIDS and Herpes infections, comprising:
   contacting a surface or cavity which is infected with an envelope virus with an antiviral formulation, which comprises:
   humectant in a concentration of from about 20% to about 80%; and
   activating agents including inorganic monovalent anions and detergent, wherein the formulation is contacted to the infected surface or cavity by a carrier or dispenser.

2. The method recited in claim 1, whereby said inorganic monovalent anions comprise bicarbonate anions.

3. The method recited in claim 2, wherein said inorganic monovalent anions further comprise thiocyanate anions.

4. The method recited in claim 2, whereby said inorganic monovalent anions are further selected from the group consisting of thiocyanate, chloride and fluoride ions.

5. The method recited in claim 3, wherein said thiocyanate ion comprises sodium thiocyanate.

6. The method recited in claim 1, wherein said detergent comprises anionic surfactant detergent.

7. The method recited in claim 1, wherein said detergent comprises non-ionic surfactant detergent.

8. The method recited in claim 6, wherein said detergent further comprises non-ionic surfactant detergent.

9. The method recited in claim 8, wherein said anionic surfactant detergent is selected from the group consisting of sodium lauryl sarcosinate, and sodium lauryl sulfate.

10. The method recited in claim 7, wherein said non-ionic surfactant detergent is selected from the group consisting of Tween 20, polymers of polyoxyethylene, and polymers of polypropylene.

11. The method recited in claim 1, wherein said humectant is selected from the group consisting of glycerol, sorbitol, glycol, sugar alcohols, and corn syrup.

12. The method recited in claim 11, wherein said humectant is present in the concentration of from about 30% to about 50%.

13. The method recited in claim 1, wherein said humectant is glycerol in a concentration of about 40%.

14. The method recited in claim 4, wherein said humectant sorbitol in a concentration of about 30%.

15. The method recited in claim 12, in which said contacting step includes introducing said antiviral formulation into the oral, vaginal or anal cavity.

16. The method recited in claim 15, in which said antiviral formulation further comprises an antimicrobial agent, including chlorhexidine at a concentration from about 0.01% to 0.2% v/v.

17. The method recited in claim 1, wherein said antiviral formulation includes said bicarbonate ion in a concentration from about 0.5% to about 5%, said anionic surfactant detergent in a concentration of 0.05% to about 1% and said non-ionic surfactant detergent in a concentration from about 0.1% to about 3%.

18. The method recited in claim 17, wherein said humectant comprises glycerol, said bicarbonate ion comprises sodium bicarbonate; said anionic surfactant detergent is selected from the group consisting of sodium lauryl sarcosinate and sodium lauryl sulfate, said non-ionic surfactant detergent is selected from the group consisting of Tween 20, polymers of polyoxyethylene, and polymers of polypropylene; and
   said humectant further comprising inorganic monovalent anions, selected from the group consisting of thiocyanate, chloride and fluoride ions in a concentration from about 0.5% to about 5%.

19. The method recited in claim 18, wherein said inorganic monovalent anion comprise sodium thiocyanate; said ionic surfactant detergent comprises sodium lauryl sarcosinate; and said non-ionic surfactant detergent comprises Tween 20.

20. The method recited in claim 18, wherein said humectant comprises sorbitol in a concentration from about 20% to about 50%.

21. The method recited in claim 18, wherein said humectant is glycerol in a concentration of about 40%.

22. The method recited in claim 20, wherein said humectant is sorbitol in a concentration of about 30%

23. The method recited in claim 17, wherein said antiviral formulation further comprises sweetening, coloring and/or flavoring agents.

24. The method recited in claim 18, wherein said antiviral formulation is formulated into the group. selected from an oral rinse, a mouth spray, a toothpaste gel composition, a toothpaste, a chewing gum, a breath freshener tablet, a candy, a lozenge, a denture cleanser, a denture adhesive, a vaginal cream, a vaginal suppository, an anal cream, an anal suppository, and a spermicide.

* * * * *